US012797051B2

(12) United States Patent
Smith et al.

(10) Patent No.: US 12,797,051 B2
(45) Date of Patent: Nov. 17, 2026

(54) CYTOLOGY BRUSH SYSTEMS AND RELATED METHODS

(71) Applicant: Boston Scientific Scimed, Inc., Maple Grove, MN (US)

(72) Inventors: Paul Smith, Smithfield, RI (US); Scott E. Brechbiel, Burlington, MA (US); Andrew James Schaubhut, Bolton, MA (US); Narunn Suon, Lawrence, MA (US); Tony Soukalopoulos, Worcester, MA (US); Naomi Gannon, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 210 days.

(21) Appl. No.: 18/796,486

(22) Filed: Aug. 7, 2024

(65) Prior Publication Data

US 2025/0049420 A1 Feb. 13, 2025

Related U.S. Application Data

(60) Provisional application No. 63/518,342, filed on Aug. 9, 2023.

(51) Int. Cl.
*A61B 10/02* (2006.01)

(52) U.S. Cl.
CPC ...... *A61B 10/02* (2013.01); *A61B 2010/0216* (2013.01)

(58) Field of Classification Search
CPC ........................ A61B 10/02; A61B 2010/0216
See application file for complete search history.

(56) References Cited

U.S. PATENT DOCUMENTS

| | | | | |
|---|---|---|---|---|
| 5,201,323 A * | 4/1993 | Vermeulen | A61B 10/02 | 600/569 |
| 5,535,756 A * | 7/1996 | Parasher | A61B 10/02 | 600/570 |
| 5,702,413 A * | 12/1997 | Lafontaine | A61M 25/0043 | 606/191 |
| 6,093,155 A * | 7/2000 | Ouchi | A61B 10/04 | 606/205 |
| 2009/0299222 A1 | 12/2009 | Yanuma | | |
| 2014/0088459 A1* | 3/2014 | Roush | A61B 10/04 | 600/569 |
| 2015/0320406 A1* | 11/2015 | Sethi | A61B 10/04 | 600/565 |
| 2018/0021027 A1* | 1/2018 | Fleury | A61B 10/04 | 600/570 |

FOREIGN PATENT DOCUMENTS

| | | |
|---|---|---|
| CN | 113 440 180 A | 9/2021 |
| JP | 2004-135945 A | 5/2004 |

* cited by examiner

*Primary Examiner* — Daniel L Cerioni
(74) *Attorney, Agent, or Firm* — Bookoff McAndrews PLLC

(57) ABSTRACT

A cytology brush including a base wire having a distal end; at least one coiled loop; and a plurality of bristles. The coiled loop is configured to at least partially surround a portion of a guide wire such that the cytology brush is longitudinally movable along and adjacent to the guide wire.

20 Claims, 15 Drawing Sheets

CYTOLOGY BRUSH SYSTEMS AND RELATED METHODS

CROSS-REFERENCE TO RELATED APPLICATIONS

This application claims the benefit of priority to U.S. Provisional Application No. 63/518,342, filed on Aug. 9, 2023, which is incorporated by reference herein in its entirety.

TECHNICAL FIELD

Aspects of this disclosure generally relate to cytology brush systems and related methods. In particular, aspects of this disclosure relate to cytology brushes configured to be guided by guide wires and methods of using such cytology brushes.

BACKGROUND

Analyzing cell samples can be a helpful tool in the diagnosis and treatment of disease. Undiagnosed pain, unusual symptoms, unusual or abnormal samples, or other factors can require further investigation, and such investigation often necessitates using advanced medical devices. Medical devices, such as cytology brushes or other suitable devices, may be employed for a variety of diagnostic and surgical procedures. Many of these procedures involve delivering the cytology brush to an internal stricture (e.g., a biliary stricture) using a wire guided catheter. Diagnosis procedures often involve the removal of a portion of suspected cancerous tissue by collecting a sample of a mucosal tissue layer off the surface of a lumen within the biliary track. Diagnosing biliary strictures, done typically with cytology brushes, can be difficult because of a low cancer sensitivity rate, which can produce a false-negative diagnosis during an endoscopic retrograde cholangiopancreatography (ERCP) procedure. Low sensitivity is frequently linked to inadequate tissue sampling, which can be a limiting factor in the detection of potential malignancy.

Many existing brushes are wire guided brushes, but brushes may be unable or have difficulty entering or crossing a stricture. For example, a tip of the brush includes radially or outward extending bristles, which may redirect or otherwise impede the delivery or movement of the brush. In some cases, a brush may be inadvertently delivered to a dilated region or pocket in front of (e.g., proximal of) a stricture. As such, the brush may not be able to collect sufficient sample for proper diagnosis.

The devices and methods of this disclosure may help to rectify one or more of the deficiencies described above or address other aspects of the art. It is to be noted, however, that the scope of subject matter of this application is defined by the features listed in the claims, and not an ability to rectify any particular deficiency.

SUMMARY

Examples of this disclosure relate to, among other things, a cytology brush, comprising a base wire having a distal end; at least one coiled loop; and a plurality of bristles. The coiled loop is configured to at least partially surround a portion of a guide wire such that the cytology brush is longitudinally movable along and adjacent to the guide wire.

In another embodiment, the cytology brush comprises two coiled loops, and wherein each of the coiled loops is configured to surround at least a portion of the guide wire and configured to guide the cytology brush along the guide wire.

In yet another embodiment, the two coiled loops are arranged as a distal coiled loop and a proximal coiled loop, and wherein the distal coiled loop and the proximal coiled loop are physically coupled by a support bridge extending between the distal coiled loop and the proximal coiled loop.

In yet another embodiment, the base wire is a wound wire formed by two strands, and the distal coiled loop and the proximal coiled loop are each formed by two half loops formed from different ones of the two strands of the wound, two-strand wire.

In yet another embodiment, the two half loops are biased toward one another to bias the distal coiled loop and the proximal loop coiled loop in a closed position.

In yet another embodiment, the two strands of the wound, two-strand wire each comprise a leading end, and wherein the leading end of the two strands is welded to the base wire at a location proximal of the distal end of the base wire.

In yet another embodiment, the base wire includes a bend separating first and second portions, wherein the first and second portions of the wire are at least partially wound around each other, and a length of the two coiled loops are arranged in parallel along a length of the base wire and each of the two coil loops is formed from one portion of the first and second portions of the wire.

In yet another embodiment, the coiled loop extends substantially perpendicularly from the base wire.

In yet another embodiment, the coiled loop is at the distal end of the base wire.

In yet another embodiment, the coiled loop is a half loop configured to receive the guide wire at a non-parallel angle relative to the base wire.

In yet another embodiment, the base wire further includes a gap between an extreme end of a strand of the base wire, the gap being sized with respect to the guide wire such that a distance between the extreme end and the base wire allows passage of the guide wire.

In yet another embodiment, the bristles are made of rubber or silicon.

In yet another embodiment, the bristles are positioned between strands of the base wire and held in place via a friction fit.

In yet another embodiment, the bristles are made of stainless steel.

In yet another embodiment, the bristles are flexible.

In yet another embodiment, a medical device system includes a catheter comprising a lumen; a cytology brush, wherein the cytology brush includes: a base wire; and a plurality of bristles coupled to a distal portion of the base wire. The base wire and the cytology brush are moveable positioned within the lumen of the catheter, and wherein the base wire comprises at least one loop portion that is configured to at least partially surround a portion of guide wire to removably couple the base wire to the guide wire.

In yet another embodiment, the base wire includes a bend separating first and second portions, wherein the first and second portions of the wire are at least partially wound around each other and the base wire surrounds the guide wire at the at least one loop portion that includes a distal loop and a proximal loop; and the distal loop and the proximal loop are each formed by two half loops formed from one of the first or second portions of the base wire.

In yet another embodiment, each of the two first and second portions of the base wire comprise a leading end, and wherein the leading end of the two portions is welded to the base wire at a location proximal of a distal end of the base wire.

In yet another embodiment, a cytology brush system includes a guide wire; a cytology brush comprising a base wire and a plurality of bristles coupled to the base wire; and a catheter comprising a lumen for receiving the cytology brush. The base wire comprises at least one loop configured to at least partially surround the guide wire and removably couple the base wire to the guide wire for insertion of the cytology brush within a patient.

In yet another embodiment, the at least one loop is a half loop configured to receive the guide wire at a non-parallel angle relative to the base wire, and the base wire further includes a gap between an extreme end of a strand of the base wire, the gap being sized with respect to the guide wire such that a distance between the extreme end and the base wire allows passage of the guide wire.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Reference will now be made in detail to examples of this disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. As used herein, the terms "comprises," "comprising," "having," "includes," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 1A:
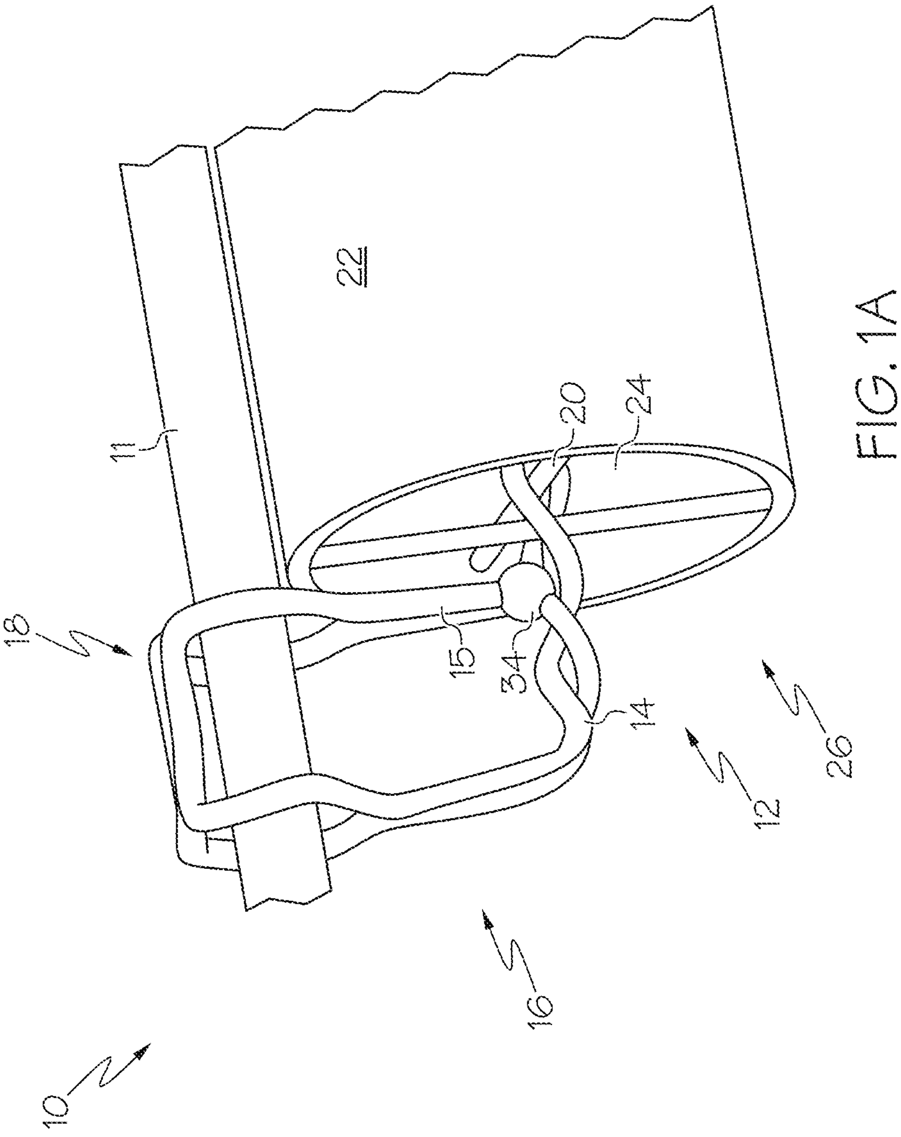
FIG. 1A illustrates an exemplary medical device system, including a medical device, according to aspects of this disclosure.
Figure 1B:
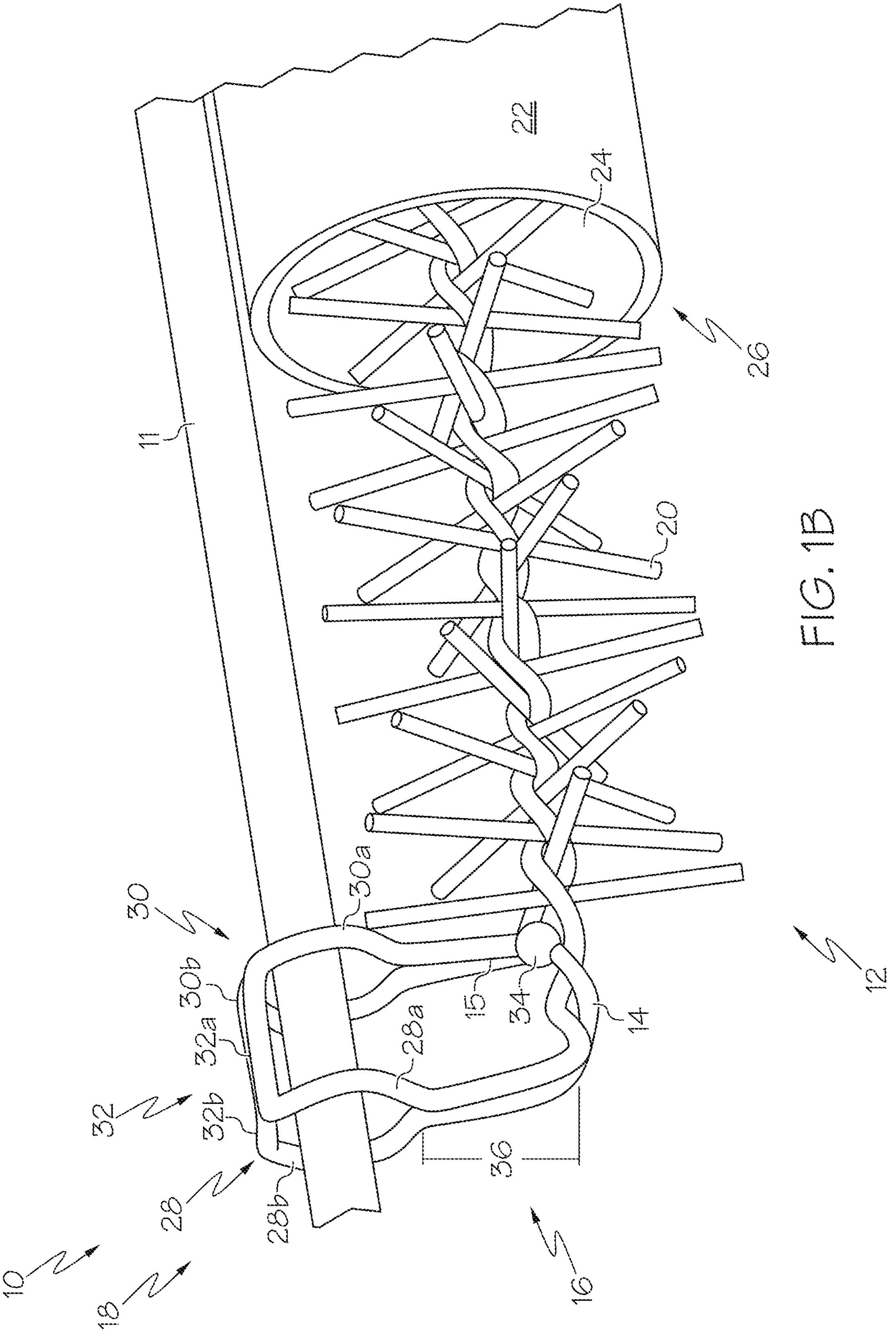
FIG. 1B illustrates the exemplary medical device system of FIG. 1A in another configuration.
Figure 1C:
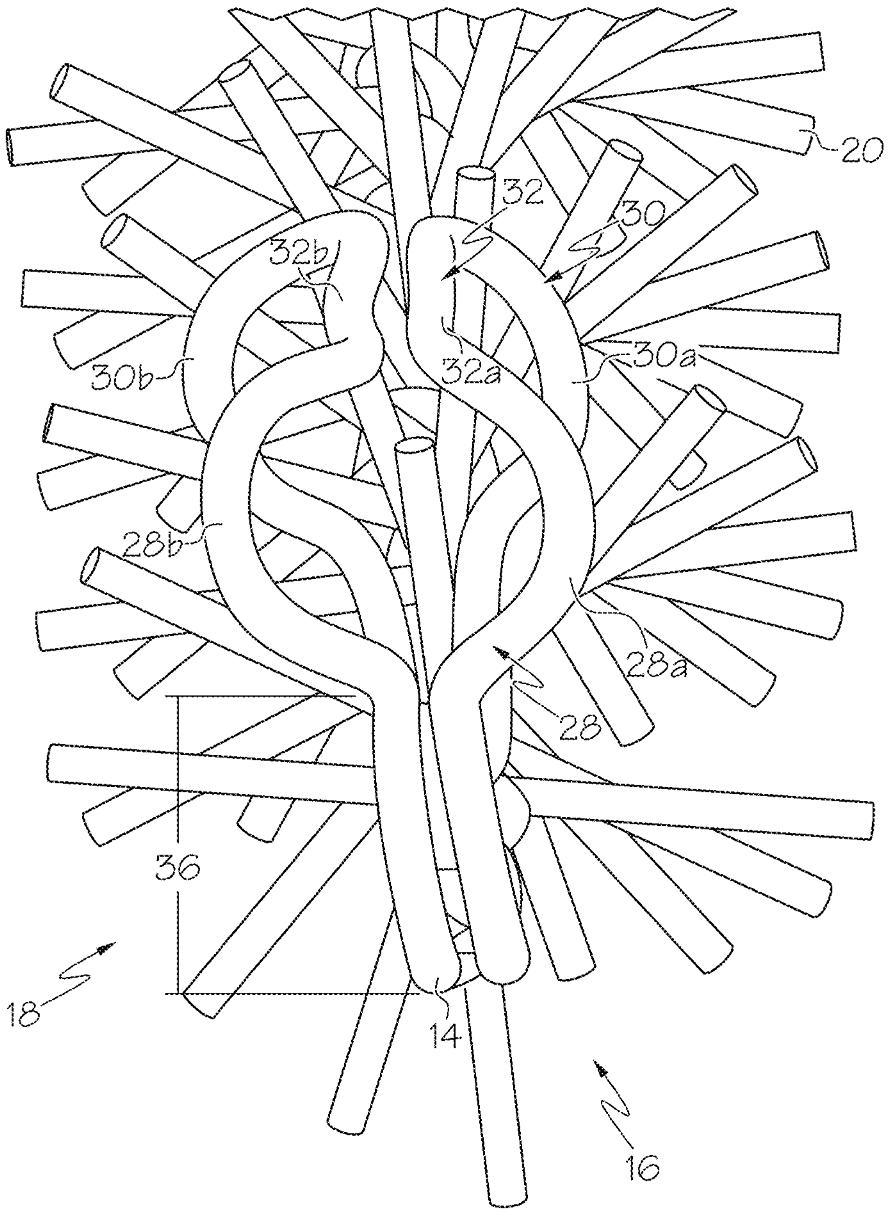
FIG. 1C illustrates a perspective end view of the medical device of FIGS. 1A and 1B.

FIG. 1A, FIG. 1B, and FIG. 1C depict various aspects of a cytology brush 12 (or "brush 12") that may be a part of a medical device system 10. In some aspects, the medical device system 10 also includes one or more of a guide wire 11 and a sheath or catheter 22. As shown, various portion(s) of the brush 12 may be configured to fit over the guide wire 11. Additionally, various portions of the brush 12 may be surrounded by or otherwise enclosed within a sheath or catheter 22, and the brush 12 may be movable relative to one or more of the guide wire 11 and/or the catheter 22, for example, along a portion of the guide wire 11 and/or within a lumen 24 of the catheter 22.

The brush 12 (or simply "brush" 12) that includes a flexible base wire 14 with a distal end 16. A portion of the brush 12 may be configured to around or over a portion of the guide wire 11. The base wire 14 may be a brush-carrying base wire and may be formed (e.g., bent, shaped, etc.) such that it forms at least one loop structure 18 in the brush 12, for example, the loop structure 18 may include one or more coils. The base wire 14 may generally form a helical structure, which may be formed from a single or multiple wire strands (e.g., a single wire strand that is bent at an end of the wire to form two overlapping portions and those overlapping portions are wound together to form the base wire 14). In some examples, the brush 12 may include two generally parallel, wound strands or wires The base wire 14 may be made of a suitably pliable and strong material such as, for example, stainless steel, copper, nickel, and/or one or more other materials. In any of these examples, the base wire 14 of the brush 12 may extend through an endoscope or other insertion device and may be manipulable by a user (e.g., a physician controlling the insertion device) to move the base wire 14, including the brush 12, within a patient. In some aspect, the user may also control or otherwise manipulate one or more other components of the medical device system 10 (e.g., the guide wire 11 and/or the catheter 22) within the patient. In some embodiments, the brush 12 may pass in and out of the patient through the catheter 22, which may include the lumen 24. In other embodiments, the catheter 22 may be removed with the brush 12.

The brush 12 also includes a plurality of bristles 20, as shown in more detail in FIG. 1B. In one or more embodiments, the bristles 20 may be formed of any suitable material such as, for example, stainless steel, copper, nickel, rubber, silicon, and/or one or more other materials. The brush 12 may generally be used to collect tissue samples from the body of a patient using the bristles 20. In some aspects, the guide wire 11 may be positioned within the patient, for example, within or adjacent to a portion of the biliary track (e.g., within a stricture). A portion of the brush 12 may be positioned over the guide wire 11, and the brush 12 (e.g., with the catheter 22) may be delivered within the patient, with the guide wire 11 helping deliver and/or position the brush 12.

For example, with the brush 12 positioned within the patient (for example, inserted into a portion of a biliary track), at least a portion of the brush 12 may be extended distally of the catheter 22, exposing at least some of the bristles 20. The bristles 20 may contact the internal tissue of the patient to collect cells and/or other tissue. For example, the brush 12 may be incrementally distally extended and/or proximally retracted, such that the bristles 20 contact and collect cells and/or other tissue. After collecting the cells and/or other tissue, the brush 12 may then be retracted proximally into the lumen 24 of the catheter 22. The brush 12 (e.g., with the catheter 22) may be retracted from the patient (e.g., with the catheter enclosing the brush 12 and its bristles 20), and the tissue may be collected from the bristles 20 and tested to make one or more diagnoses (e.g., a cancer screening, etc.)

As mentioned above, the brush 12 may be slidably couplable such that it can pass in and out of the patient through the catheter 22 (e.g., through the lumen 24 extending through a length of the catheter 22). The embodiment depicted includes the guide wire 11 outside (e.g., radially outside or external of) the catheter 22. However, in some embodiments, the catheter 22 surrounds both the guide wire 11 and the brush 12, and each of the guide wire 11, the brush 12, and the catheter 22 may be moveable with respect to the other components of the medical device system 10. The brush 12 may be inserted into the catheter 22 at a proximal end (not shown) of the catheter 22. Alternatively, the brush 12 and may be inserted into a distal end 26 of the catheter 22. If the guide wire 11 is positioned within the lumen 24 of the catheter 22, the guide wire 11 may be inserted into the catheter at the proximal end or at the distal end 26. In any of these aspects, the brush 12 (either with the guide wire 11 or separate from the guide wire 11) can pass through the catheter 22 and extend from the distal end 26 of the catheter 22 to reach a treatment site in the patient. The brush 12 and catheter 22 may pass through the patient guided by the guide wire 11. The catheter 22 may help to form or otherwise provide an atraumatic transport mechanism for the brush 12, for example, by enclosing at least a majority of the bristles 20 and can help to retain and/or protect tissue sample (e.g., cells) collected with the brush 12 as it is removed.

As shown in FIG. 1A and FIG. 1B, the loop structure 18 may be formed by one or more portions of the flexible base wire 14 and the one or more portions may surround the guide wire 11 to mount or otherwise couple the brush 12 with the guide wire 11. As depicted in FIG. 1B, the loop structure 18 can include a distal loop 28 and a proximal loop 30 that are physically coupled by a support bridge 32. The distal loop 28, the proximal loop 30, and the support bridge 32 may be formed by bending individual (that is, the base wire 14 may include a bend separating one or more portions), continuous strands of the base wire 14 into portions of or half loops (28*a*, 28*b* and 30*a*, 30*b*) and positioning corresponding or cooperating half loops next to one another to form an entire loop, such as the distal loop 28 and the proximal loop 30. The half loops (28*a*, 28*b* and 30*a*, 30*b*) may be moved into proximity with one another, such that the guide wire 11 cannot fit between the two respective half loops and the two adjacent portions of the support bridge 32 (32*a*, 32*b*), thus helping to maintain a coupling between the brush 12 and the guide wire 11. In some embodiments, the stiffness of the material used to form the loop structure 18 may help bias the half loop portions 28*a*, 28*b*, and 30*a*, 30*b* toward one another, such that loop structure 18 is biased toward enclosing the guide wire 11 when the brush 12 is coupled to the guide wire 11 (e.g., the loop structure 18 can "clip" the brush 12 around the guide wire 11).

In some embodiments, the half loop structures (28*a*, 28*b* and 30*a*, 30*b*) may be fitted onto and/or around the guide wire 11 outside of a patient's body and then may be manipulated such that the half loop structures, along with the brush 12, are advanced along the longitudinal length of the guide wire 11 to a treatment site (e.g., a stricture). That is, the guide wire 11 may already be positioned in the patient during a procedure, and the brush 12 (or the brush 12 and catheter 22) may be moved longitudinally along the guide wire 11 to the treatment site.

The base wire 14 may generally end at the leading edges 15, which may form a junction between the furthest possible ends of the base wire 14 and a more proximal portion of the base wire 14. In some embodiments, the leading ends 15 of the one or more of the individual strands may be fixedly coupled to the base wire 14, for example, at a weld 34. The weld 34 may help to support or otherwise maintain the structural integrity of the loop structure 18. The loop structure 18 may be offset (e.g., laterally offset) from the base wire 14 by a lateral offset portion 36. The lateral offset portion 36 may be formed from individual strands (e.g., unwound portions) of the base wire 14 and may help to provide clearance or spacing between the guide wire 11 and the base wire 14 of the brush 12. The clearance or spacing may help to ensure that the bristles 20 or other portions of the brush 12 are do not contact the guide wire 11. The clearance or spacing may also help to ensure that the guide wire 11 does not contact or otherwise interfere with the bristles 20 and/or the longitudinal motion of the brush 12, for example, as the bristles 20 of the brush 12 contact and collect tissue/cell samples. The spacing may also help to provide clearance between the catheter 22 and the guide wire 11.

As shown in FIG. 1A and FIG. 1B, the loop 18 may surround a portion of the guide wire 11, which may help to ensure that brush 12 is secured to the guide wire 11 during the passage of the brush 12 to the correct location within the patient. In some embodiments, the loop 18 may ride along the guide wire 11, guided by the guide wire 11, such that the loop 18 guides the brush 12 (and thus also the catheter 22) to the treatment site. The brush 12 may slide longitudinally along and adjacent to the guide wire 11, with the guide wire 11 guiding the brush 12, for example, to the treatment site. For example, at the location of a stricture, the brush 12 may extend from the lumen 24 of the catheter 22 without relative motion between the catheter 22 and the guide wire 11 to expose the brush 12 and thereby collect a tissue sample. In other embodiments, the catheter 22 may be retracted, exposing the brush 12. The guide wire 11 may remain in place with respect to a stricture, while the brush 12 may move longitudinally with respect to the lumen 24 such that the brush 12 may collect a sample, coming into contact with the tissue of the patient. In other embodiments, the catheter 22 may be retracted to expose the bristles 20 of the brush 12 without longitudinal movement of the brush 12 with respect to guide wire 11 and thereby collect a sample. FIG. 1B shows the brush 22 in a longitudinally advanced (e.g., distally extended) position with respect to the catheter 22 (e.g., extending from the catheter 22). Once a sample is collected, the brush 12 and/or the catheter 22 may be removed from the patient, as controlled by the user.

Figure 2:
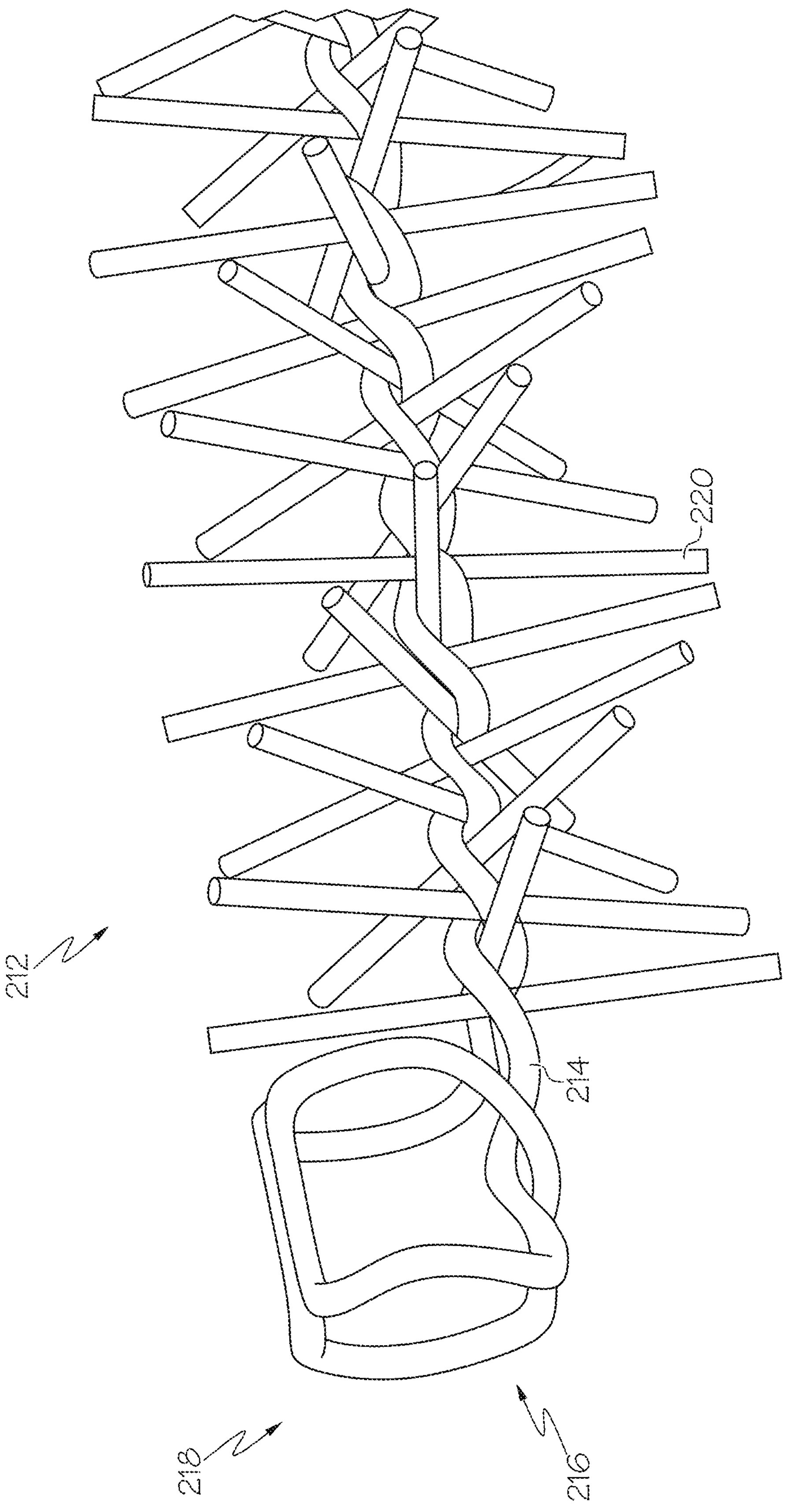
FIG. 2 illustrates another exemplary medical device.

FIG. 2 depicts an embodiment including one or more features of a medical device system including a medical device in the form of a brush 212 that does not include a lateral offset from the guide wire 11 (not depicted). As shown, the brush 212 includes a loop structure 218 formed at a distal end 216 from individual strands or portions of a base wire 214. The brush 212 also includes a plurality of bristles 220. As discussed above, the loop structure 218 may receive and/or ride along a guide wire (e.g., the guide wire 11). In such an embodiment, the brush 212 would slide along the guide wire 11 with the base wire 214 adjacent to the guide wire 11. As such, a portion of one or more of the bristles 220 of the brush 212 may surround one or more portions of the guide wire 11. In such an embodiment, the bristles 220 may be sized to extend beyond a diameter of the guide wire 11, for example, such that the bristles 220 may contact the tissue of a patient even if the tissue of the patient is on an opposite side of the guide wire 11 from the brush 212 (e.g., if the guide wire 11 is positioned between the brush 212 and the tissue). For example, the length of one or more of the bristle 220 (i.e., extending from the base wire 214 to the end of the bristle 220) may be at least slightly longer than the diameter of the guide wire 11.

Figure 3A:
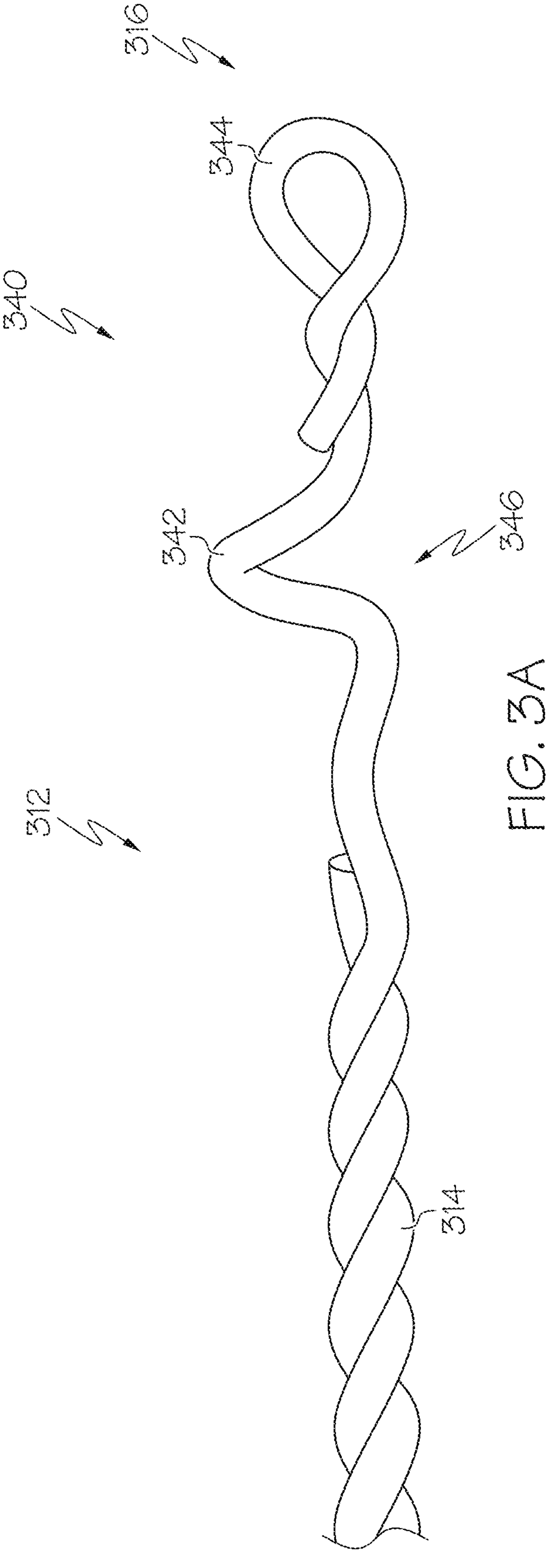
FIG. 3A illustrates yet another exemplary medical device.
Figure 3B:
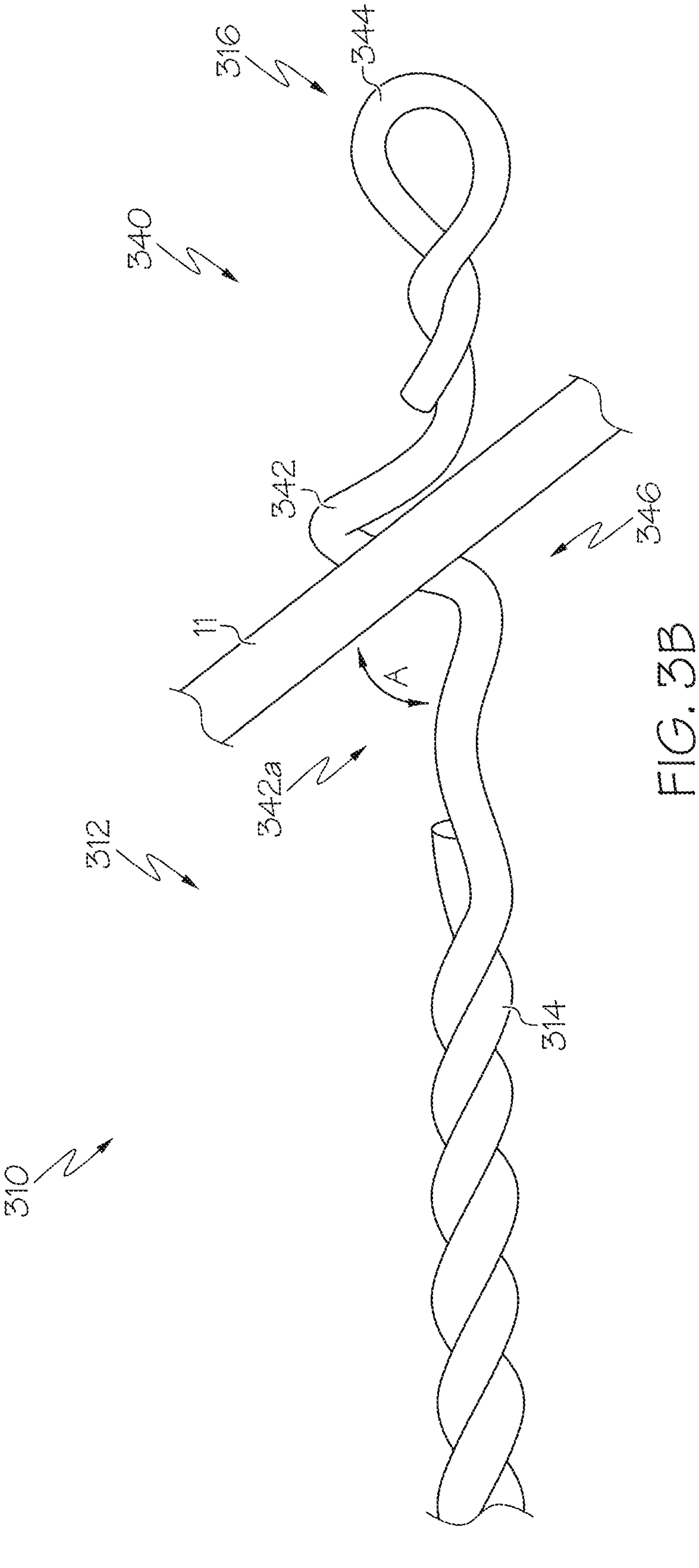
FIG. 3B illustrates a medical device system, including the medical device of FIG. 3A and a guide wire, in a first configuration.
Figure 3C:
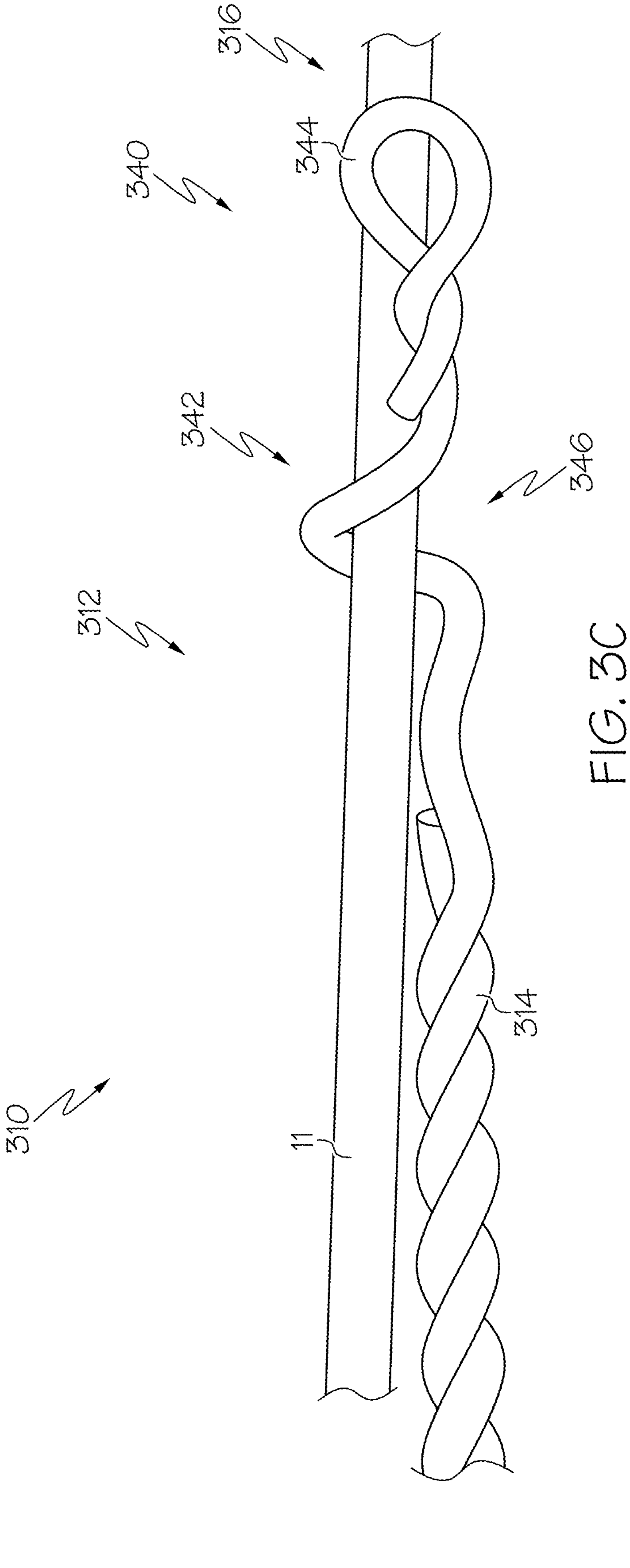
FIG. 3C illustrates the medical device system of FIG. 3B in a second configuration.

FIG. 3A, FIG. 3B, and FIG. 3C depict various aspects of another brush 312, for example, forming another medical device system 310 including a guide wire 11 (FIGS. 3B and 3C). As shown, the brush 312 includes a loop structure 340 including an open loop 342 and a closed loop 344. The open loop 342 and the closed loop 344 may be formed from a base wire 314 for removably and slidably coupling the brush 312 with the guide wire 11. The exemplary brush 312 depicted in FIG. 3A-3C does not include bristles for clarity, but it is noted that embodiments may include bristles distal or proximal to the open loop 342 and/or proximal to the closed loop 344.

FIG. 3B and FIG. 3C depict various aspects of coupling the guide wire 11 with the brush 312. That is, the guide wire 11 and the brush 312 may be arranged relative to one another (e.g., at a non-parallel angle) such that a portion of the guide wire 11 fits within the open portion 342*a* of the loop formed by the open loop 342. Then, the guide wire 11 and/or the brush 312 may be moved relative to one another (e.g., in the directions shown by arrow A) such that the open loop 342 slidably fits around the guide wire 11. In some embodiments, a size (e.g., a radius) and/or a shape of the open loop 342 may be configured such that a portion or all of the base wire 314 forming the open loop 342 forms a friction fit with the guide wire 11. That is, the brush 312 may fit (e.g., snap) onto the guide wire 11, as shown in FIG. 3C. In these aspects, the brush 312 may move longitudinally along the guide wire 11 but not substantially laterally or in a radial outward direction with respect to a longitudinal axis of the guide wire 11. Still, the brush 312 may be configured such that the brush 312 may rotate around the guide wire 11.

The closed loop 344 may be formed at the distal end 316 of the base wire 314 and may generally form an atraumatic tip of the brush 312. In various embodiments, the closed loop 344 may or may not surround the guide wire 11. The open loop 342 and the closed loop 344 could be formed from a single strand of the base wire 314 as shown or from separate strands of the base wire 314. Some embodiments may include a cut away portion 346, which may be formed from a single wire in the base wire 314 which may make coupling between the guide wire 11 and the base wire 314 simpler by removing a potentially interfering portion of the base wire 314

Figure 4:
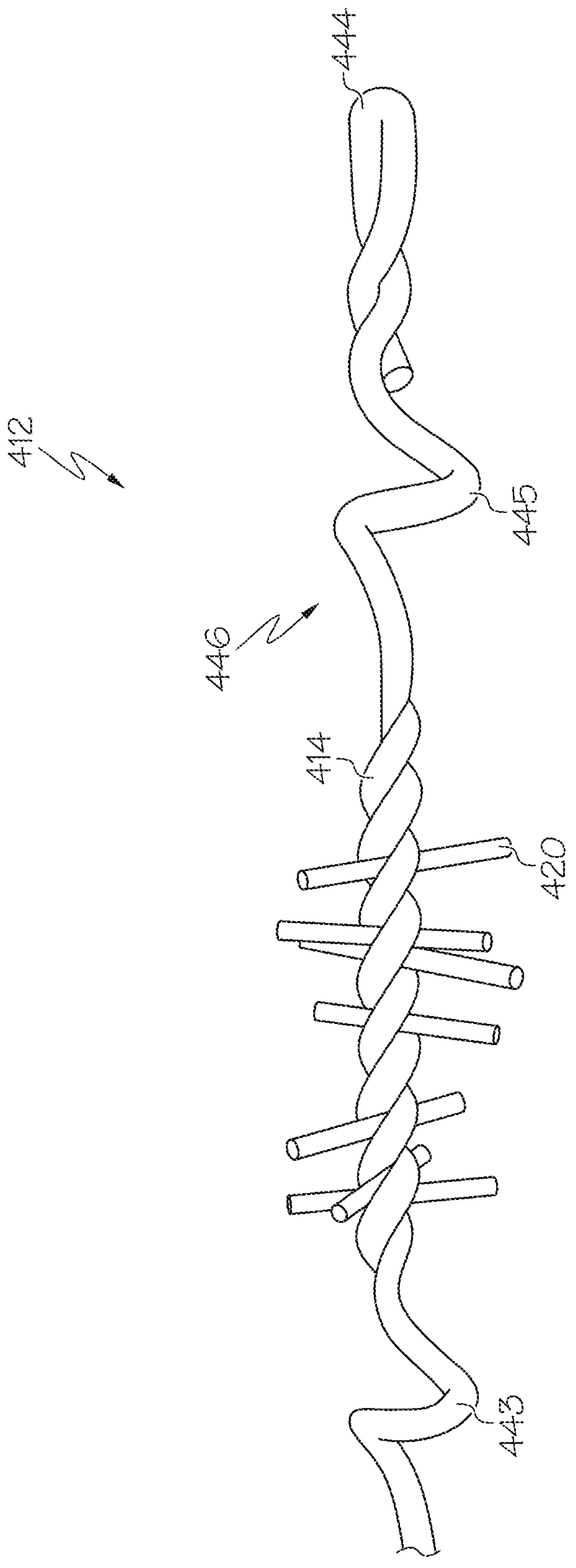
FIG. 4 illustrates another embodiment of an exemplary medical device.

FIG. 4 shows an embodiment of the medical device, for example, a cytology brush 412 that includes a base wire 414 with a proximal open loop 443, a distal open loop 445, and a closed loop 444. The closed loop 444 may be at a distal end of brush 412, as discussed above with respect to closed loop 344. The proximal open loop 443 and the distal open loop 445 may extend substantially perpendicularly from the base wire 414 and could both surround a guide wire, such as the guide wire 11 of FIG. 1A. The brush 412 of FIG. 4 includes winds in the base wire 414, and the winds may help to secure a plurality of bristles 420 to the base wire 414, for example, for collecting a tissue sample, as discussed above. As depicted, the bristles 420 may be positioned generally between the proximal open loop 443 and the distal open loop 445, but this is not required and embodiments are considered in which the bristles 420 are on a distal side and/or a proximal side of one or both of the proximal open loop 443 and the distal open loop 445. One or both of the proximal loop 443 and the distal open loop 445 can be formed such that they form a friction fit (e.g., a snap fit) with the guide wire (not shown). In these aspects, the brush 412 can move longitudinally with respect to the guide wire, but the brush 412 may be prevented from translating radially with respect to the guide wire due to the friction fit between the loop(s) and the guide wire. Still, the brush 412 may be configured such that it can rotate around the guide wire. In some embodiments, the proximal open loop 443 and the distal open loop 445 may be formed from a single strand of the base wire 414 to enable more expedient coupling between the brush 412 and the guide wire 11 (not shown). For example, the distal open loop 445 may be formed at a single strand portion 446 of the brush 412.

Figure 5:
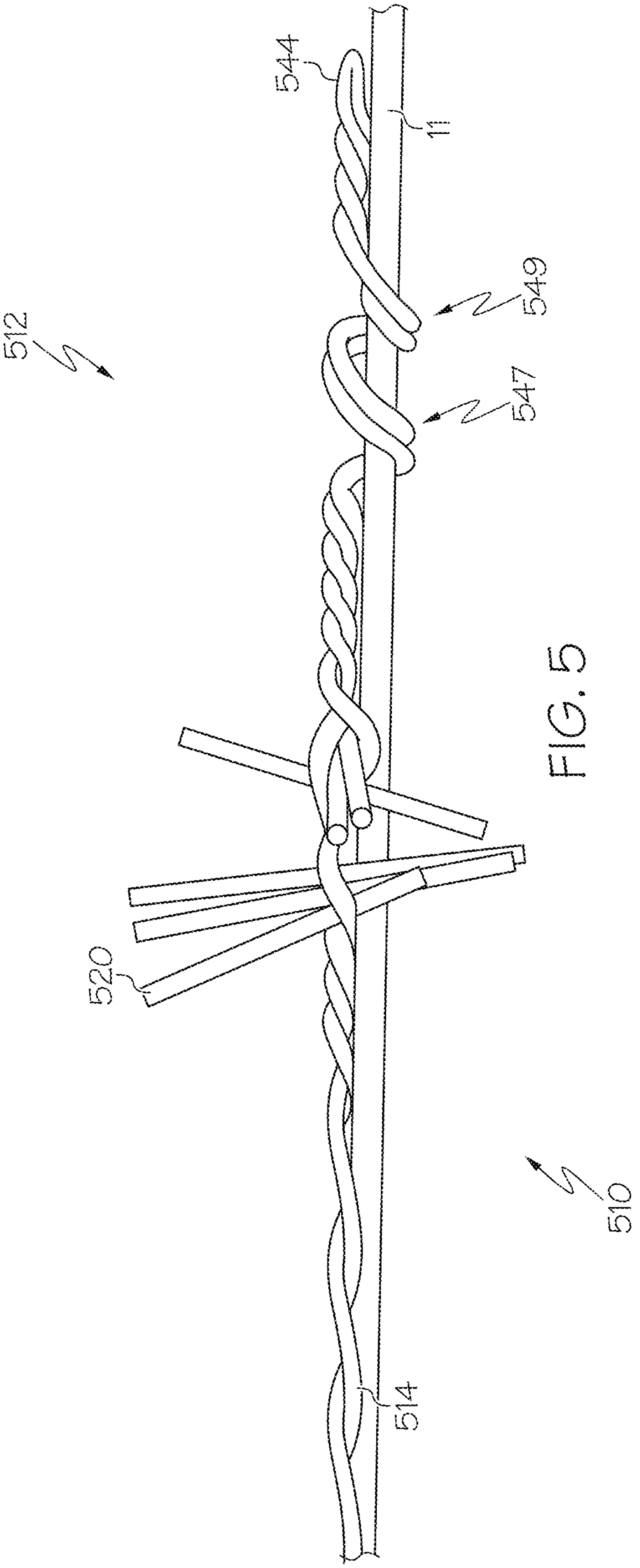
FIG. 5 illustrates another embodiment of an exemplary medical device system, including a medical device and a guide wire.

FIG. 5 shows an embodiment of the medical device system 510 including a medical device, such as a brush 512 and a guide wire 11. As shown, the brush 512 includes a base wire 514 that forms two consecutive open loops, for example, a proximal open loop 547 and a distal open loop 549. The proximal open loop 547 and the distal open loop 549 may surround the guide wire 11. Bristles 520 extend from winds in the base wire 514. A user can manipulate the brush 512 around the guide wire 11 with the brush 512 outside the patient's body such that the brush 512 is moveable with respect to a longitudinal axis of the guide wire 11 but such that the brush 512 cannot translate radially with respect to the guide wire 11. Once the brush 512 surrounds the guide wire 11, the brush 512 can be moved proximally and distally with respect to the guide wire within the patient to collect a sample. Additionally, the brush 512 may incorporate a closed distal loop 544, which may form a distal end of the brush 512.

Figure 6A:
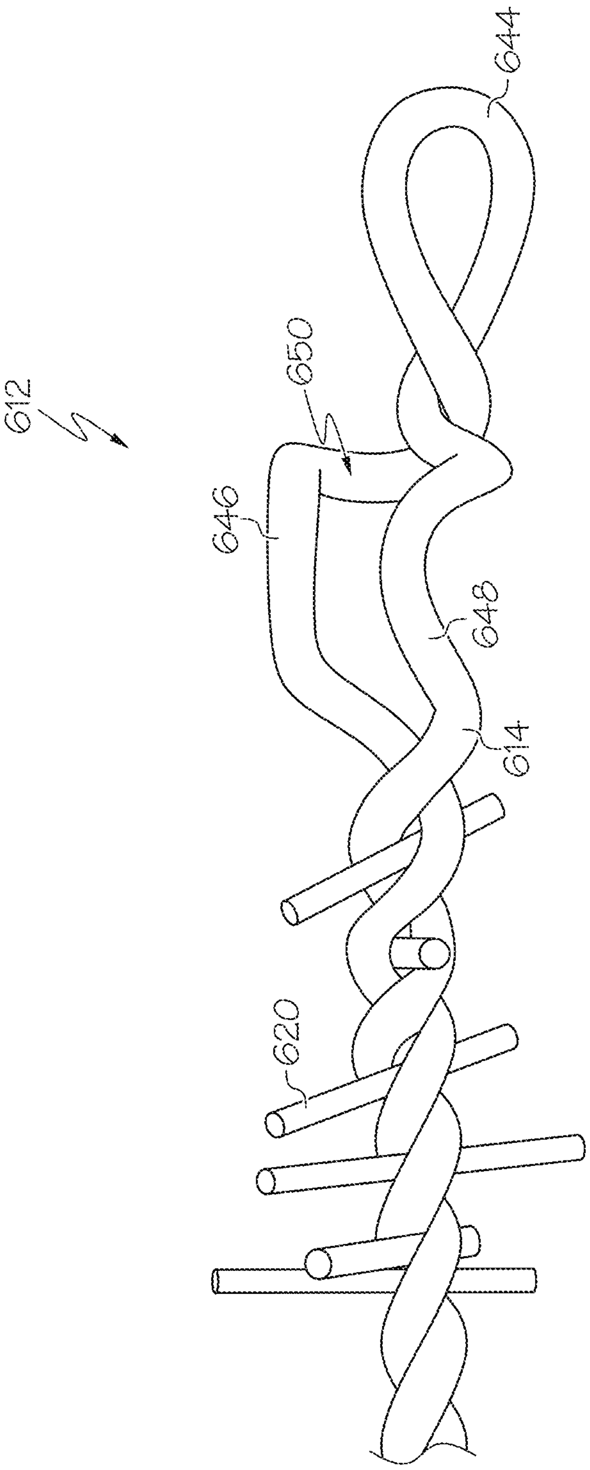
FIG. 6A illustrates another embodiment of an exemplary medical device.
Figure 6B:
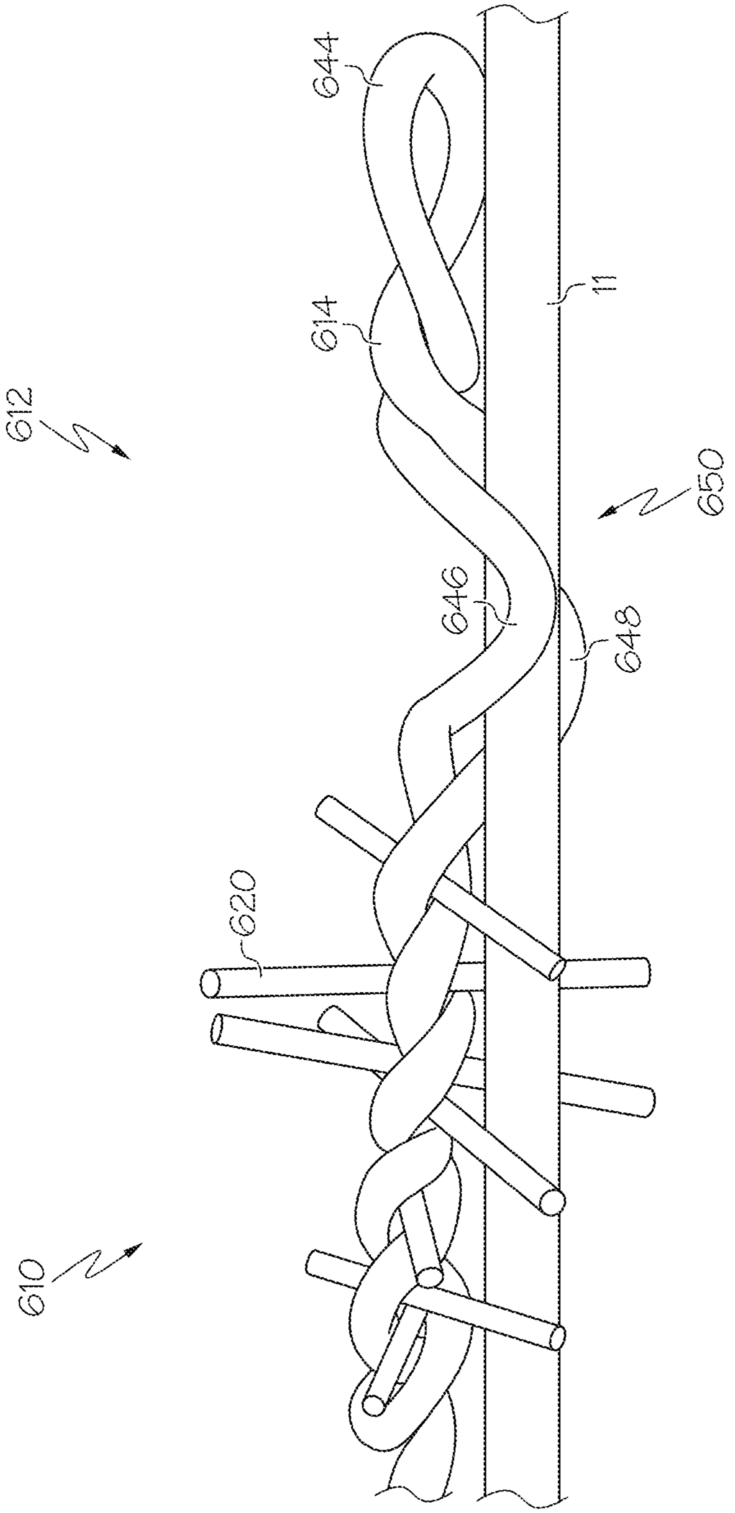
FIG. 6B illustrates a medical device system that includes the medical device of FIG. 6A and a guide wire.

FIG. 6A and FIG. 6B show another medical device or cytology brush 612 including bristles 620. As shown in FIG. 6B, the cytology brush 612 may be coupled to a guide wire 11 to form another medical device system 610. The cytology brush 612 may include a base wire 614 and a plurality of bristles 620. Additionally, the base wire 614 includes a first side loop 646 and a second side loop 648, with each of the first side loop 646 and the second side loop 648 being formed using a single strand of the base wire 614. The first side loop 646 and the second side loop 648 may be half loops of individual strands of the base wire 614 and each may be curved at a portion of the strand (e.g., a radial extremity or end) to form a space 650 for receiving the guide wire 11 (not depicted in FIG. 6A). The space 650 may be sized such that the radial extremities or ends of the first side loop 646 and the second side loop 648 are closer together than a diameter of the guide wire 11. The remaining portions of the first side loop 646 and the second side loop 648 may be spaced apart by a distance that is wider than the diameter of the guide wire 11. In these aspects, the first side loop 646 and the second side loop 648 may at least partially surround the guide wire 11 to allow the brush 612 to move longitudinally with respect to the guide wire 11. The embodiment depicted in FIG. 6A and FIG. 6B may further include a closed loop 644 to form an atraumatic tip of the brush 612, as discussed above.

Figure 7A:
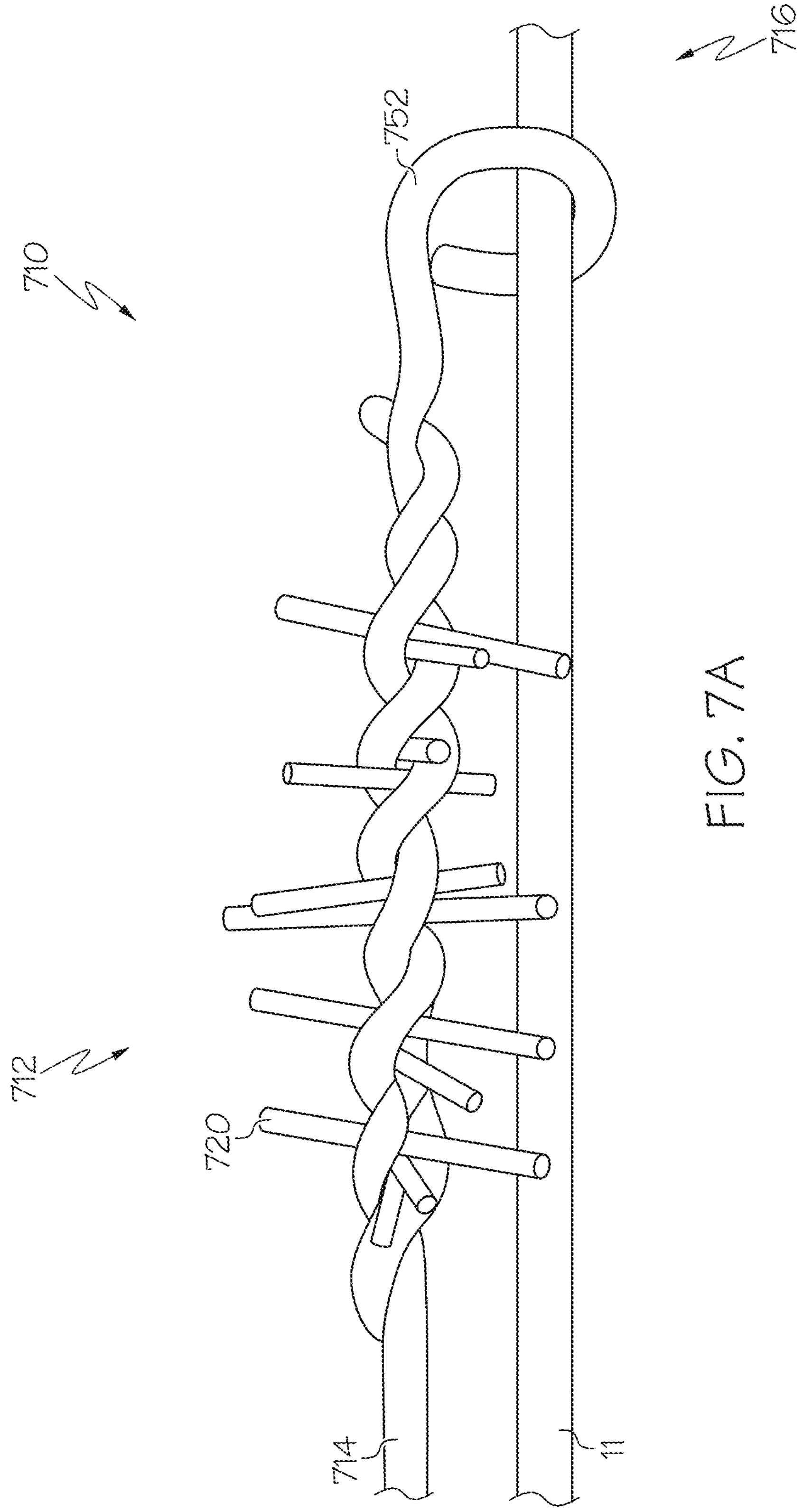
FIG. 7A illustrates a further exemplary medical device system that includes a medical device and a guide wire.

FIG. 7A depicts a medical device system 710 including an exemplary cytology brush 712 and a guide wire 11. The brush 712 includes a plurality of bristles 720 positioned within portions of a base wire 714. Additionally, the brush 712 includes a loop 752 at a distal end 760 of the base wire 714, and the loop 752 may surround a portion of the guide wire 11.

Figure 7B:
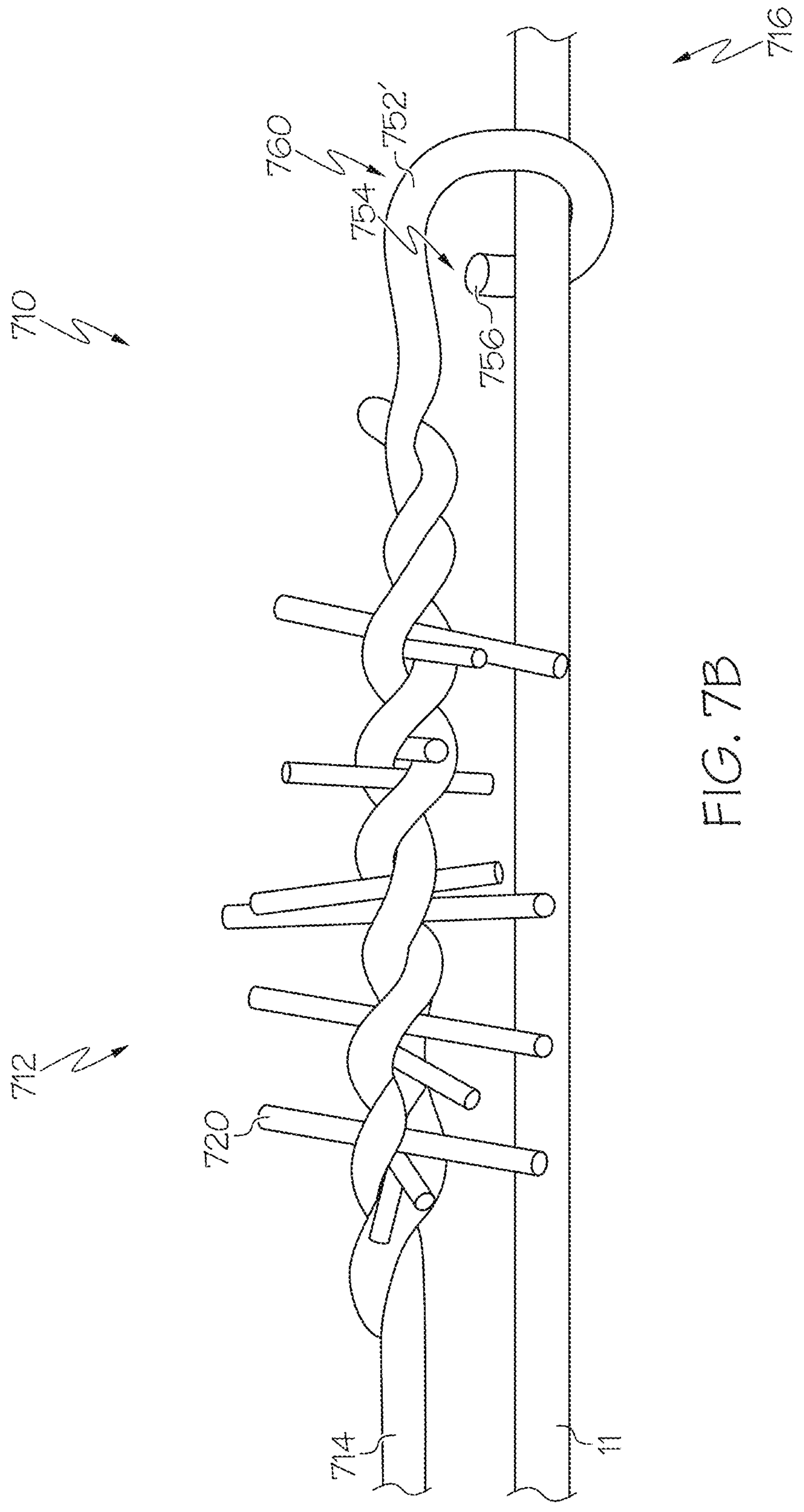
FIG. 7B illustrates another configuration of the exemplary medical device system of FIG. 7A.

FIG. 7B depicts medical device system 710 including the brush 712 and the guide wire 11. Additionally, FIG. 7B illustrates the brush 712 in a different configuration than in FIG. 7A, for example, including a loop 752'. The loop 752' may be larger (e.g., circumferentially) than the loop 752 in FIG. 7A, for example, by the user pulling or otherwise urging end 756 away from the more proximal portion of base wire 714. The loop 752' of FIG. 7B includes a gap 754 between an end 756 of a single strand of the base wire 714 forming the distal end 716 of the brush 712. The gap 754 may be sized with respect to the guide wire 11 such that a distance between the end 756 and the base wire 714 allows passage of the guide wire 11. In this aspect, a user may position the brush 712 onto the guide wire 11 at a portion along a length of the guide wire 11, that is, without the user having to slide the brush 712 onto the guide wire 11 at the longitudinal end of the guide wire 11. In some embodiments, the base wire 714 may be formed from a single strand, for example, to make coupling with the guide wire 11 simpler or to avoid interference between the brush 712 and the guide wire 11.

Figure 8:
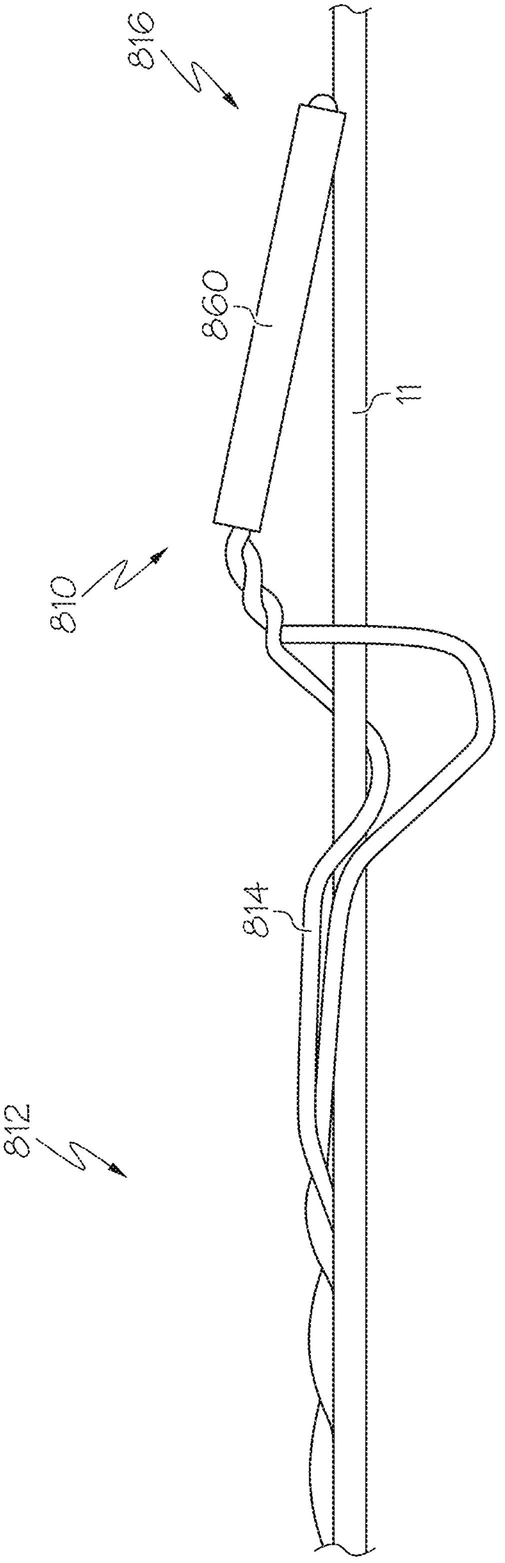
FIG. 8 illustrates another exemplary medical device system.

FIG. 8 shows an embodiment of a medical device system 810 that includes a medical device, for example, a brush 812, and a guide wire 11. At least a portion of the brush 812 may include a base wire 814, and the base wire 814 may be mounted on or otherwise coupled to one or more portions of the guide wire 11, as discussed herein. Although not shown, the medical device system 810 may include a sheath or catheter, as discussed above. Additionally, the medical device system 810 includes a tube, for example, a hypotube 860 that surrounds the base wire 814. The hypotube 860 may be made of metal, plastic, or another suitable material and may surround one or more portions of the base wire 814, such as, for example, a distal end 816 of the base wire 814. The hypotube 60 may crimp the distal most portions of the base wire 814 such that the distal most portions are atraumatic as the brush 812 is delivered through a patient along the guide wire 11 to a treatment site. As such, the hypotube 860 may help to protect the patient's tissue from unnecessary scraping or damage and ensuring a sample includes tissue from intended area(s) (i.e., the treatment site).

Figure 9:
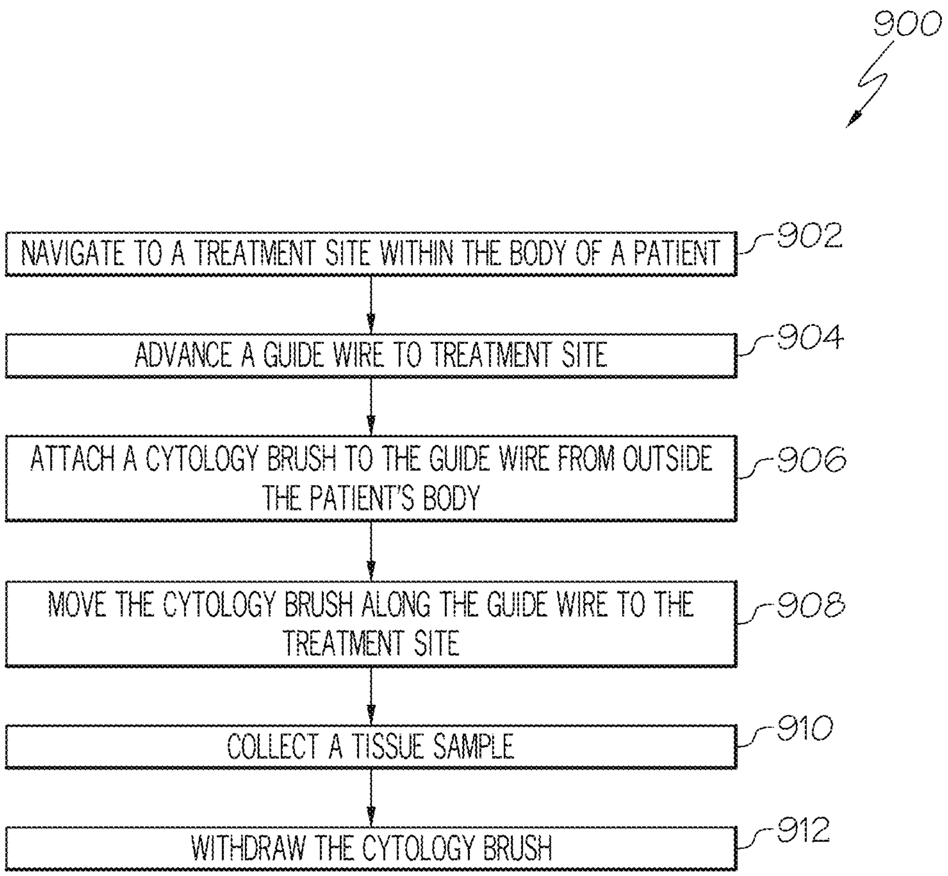
FIG. 9 illustrates a method of using an exemplary medical device system.

FIG. 9 depicts an exemplary method 900 of using one or more components of a medical device system, such as the medical device system 10 described above. An outer sheath or insertion device (e.g., an endoscope) may be inserted into the patient's body through an incision or natural orifice, and may be navigated to a treatment site at a step 902. For example, an outer sheath or insertion device may be inserted into the subject's body and navigated through the subject's body until a distal end reaches or is adjacent to the treatment site.

The guide wire 11 may be inserted into the patient, for example, along an outer surface of the outer sheath, such that the guide wire 11 is also advanced to the treatment site of the subject's body at a step 904. Alternatively, the guide wire 11 may be inserted into the body to the treatment site within a lumen or working channel of the outer sheath. A pushing force (e.g., in a distal direction) on a proximal portion of the guide wire 11 may be used to advance the guide wire 11 to the treatment site through the outer sheath. In some embodiments, the outer sheath may remain in the patient near the treatment site or along some portion of the path used to reach the treatment site. In other embodiments, the outer sheath may be removed from the patient once the guide wire 11 is in place near the treatment site.

The brush 12 may be slideably coupled to the guide wire 11 at a position outside the patient's body along a length of the guide wire 11 at a step 906. In some embodiments, the proximal end of the guide wire 11 may need to be threaded through one or more loops of the brush 12. For example, in embodiments having closed loops through which the guide wire 11 passes, for example, the embodiment depicted in 7A, the guide wire 11 may need to be threaded through a closed loop (such as the closed loop 752) in order for the brush 12 to be slideably attached to the guide wire 11. However, in other embodiments, such as the embodiment depicted in FIGS. 3A-3C, an open loop (such as the open loop 342) can be fitted around the guide wire 11 such that the brush 12 is slideably coupled to the guide wire 11 at a location along the length of the guide wire 11 without requiring that an end of the guide wire 11 be threaded through an opening or loop in a portion of the brush 12. Hence, a user of the system need not find a longitudinal end of the guide wire 11 in order to attach the brush 12 to the guide wire 11. Instead, the user may couple the brush 12 to the guide wire 11 anywhere along a length of the guide wire 11 (e.g., near an incision or orifice of the patient, for example, through which the guide wire 11 is already traversing). This may save the user from needing to manipulate a long length of the guide wire 11 in order to find a loose or proximal end of the guide wire 11.

At a step 908, the brush 12 is moved along a length of the guide wire 11 to the treatment site. For example, the user may push (i.e., proximally urge) a proximal end portion of the base wire 14 or a feature coupled to the base wire 14 that extends outside the patient. The user may push the base wire 14 until the brush 12 is at the treatment site and the bristles 20 are near a distal end of the guide wire and/or at the treatment site. In some embodiments, such as the embodiments depicted in FIG. 1A and FIG. 1B, the brush 12 and the catheter 22 may be advanced together along the guide wire 11. The catheter 22 may surround the brush 12 as the brush 12 moves through the patient, which may help to ensure that the brush 12 does not collect cells, tissue, or other material from the patient's tissues, organs, and other internal features that are not the treatment site. In some embodiments, the user may push proximal ends of the brush 12 and catheter 22 together such that the two components move together through a patient.

Once the brush 12 is positioned at the treatment site, the user may use the brush 12 to collect a sample in a step 910. For example, the brush 12 may be removed from the catheter 22 (e.g., by the brush 12 being distally extended from the catheter 22, the catheter 22 being proximally retracted from around the brush 12, or both) and the bristles 20 may be exposed to the treatment site to collect the sample at step 910. The sample may be collected by initiating relative motion between the catheter 22 and the brush 12 such that the brush 12 extends from the distal end 26 of the catheter 22 through the lumen 24 such that the bristles 20 may be moved into contact with tissue in the treatment site. For example, the proximal end of the base wire 14 may be pushed and/or pulled, rotated, etc. Additionally, the proximal end of the catheter 22 may be pushed and/or pulled, thereby causing the bristles 20 to move backward and/or forward on the tissue surface. The bristles 20 may brush against the treatment site, thereby scraping off cells, tissue, or other material from the treatment site. The sample may be held between or on bristles 20. In some embodiments, the bristles 20 may be designed (e.g., shape, material, etc.) such that the bristles collect relatively large amounts of material at the treatment site for the sample. For example, the bristles 20 may be designed such that the bristles have protrusions, recesses, or other features for collecting relatively large amounts of sample.

Once the tissue sample is collected on the bristles 20 of the brush 12, the user may withdraw the brush 12 in a step 912. For example, the user may position the brush 12 back into the catheter 22 and withdraw or otherwise remove the catheter 22 and the brush 12 from the patient at step 912. Positioning the brush 12 within the catheter 22 may help to isolate or otherwise protect the sample on the bristles 20 from other tissues, materials, fluids, etc. within the patient's body. Moreover, the brush 12 may be positioned within the catheter 22 by proximally retracting the brush 12 relative to the catheter 22, and/or by distally extending the catheter 11 relative to the brush 12. The brush 12 and the catheter 22 may be withdrawn or otherwise removed from the patient together. Additionally, the brush 12 may be uncoupled from the guide wire 11. For example, a user spread apart closed loops, open loops, or move the loops structures relative to the guide wire and then decouple the guide wire 11 from the one or more loop structures. The collected sample may be extracted from the brush 12 for analysis by separating the sample from the bristles 20. The extraction process may include, for example, rinsing the bristles 20 with a fluid to free the cells. Additionally or alternatively, the extraction process may include coupling the brush 12 to an electrical energy source and activating the electrical energy source to help cause the collected sample to be released or repelled from the bristles 20.

In some embodiments, the positioning of the outer sheath, guide wire 11, catheter 22, and cytology brush 12 may be monitored using an imaging device. For example, the endoscope or insertion device may include an imaging device at a distal end, such that the user(s) may observe one or more of the guide wire 11, the brush 12, or the catheter 22 via the imaging device. Alternatively or additionally, one or more of the guide wire 11, the brush 12, or the catheter 22 may include markers (e.g., radiopaque markers), such that the user(s) may observe the position of one or more of the guide wire 11, the brush 12, or the catheter 22 via an external imaging device (e.g., an X-ray).

Embodiments of the present disclosure may be applicable to various and different medical or non-medical procedures. In addition, certain aspects of the aforementioned embodiments may be selectively used in collaboration, or removed, during practice, without departing from the scope of the disclosure.

While principles of this disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A cytology brush, comprising:

a base wire comprising a distal end;

at least one coiled loop; and a plurality of bristles, wherein the coiled loop is configured to at least partially surround a portion of a guide wire such that the cytology brush is longitudinally movable along and adjacent to the guide wire.

2. The cytology brush of claim 1, wherein the cytology brush comprises two coiled loops, and wherein each of the coiled loops is configured to surround at least a respective portion of the guide wire and configured to guide the cytology brush along the guide wire.

3. The cytology brush of claim 2, wherein the two coiled loops are arranged as a distal coiled loop and a proximal coiled loop, and wherein the distal coiled loop and the proximal coiled loop are physically coupled by a support bridge extending between the distal coiled loop and the proximal coiled loop.

4. The cytology brush of claim 3, wherein:

the base wire is a wound wire formed by two strands, and the distal coiled loop and the proximal coiled loop are each formed by two half loops formed from different ones of the two strands of the wound, two-strand wire.

5. The cytology brush of claim 4, wherein the two half loops are biased toward one another to bias the distal coiled loop and the proximal coiled loop in a closed position.

6. The cytology brush of claim 5, wherein the two strands of the wound, two-strand wire each comprise a leading end, and wherein the leading end of the two strands is welded to the base wire at a location proximal of the distal end of the base wire.

7. The cytology brush of claim 2, wherein:

the base wire includes a bend separating first and second portions, wherein the first and second portions of the base wire are at least partially wound around each other, and a length of the two coiled loops is arranged in parallel along a length of the base wire and each of the two coiled loops is formed from one portion of the first and second portions of the base wire.

8. The cytology brush of claim 1, wherein the coiled loop extends perpendicularly from the base wire.

9. The cytology brush of claim 1, wherein the coiled loop is at the distal end of the base wire.

10. The cytology brush of claim 1, wherein the coiled loop is a half loop configured to receive the guide wire at a non-parallel angle relative to the base wire.

11. The cytology brush of claim 10, wherein the base wire further includes a gap between an extreme end of a strand of the base wire, the gap being sized with respect to the guide wire such that a distance between the extreme end and the base wire allows passage of the guide wire.

12. The cytology brush of claim 1, wherein the bristles are made of rubber or silicon.

13. The cytology brush of claim 1 wherein the bristles are positioned between strands of the base wire and held in place via a friction fit.

14. The cytology brush of claim 13, wherein the bristles are made of stainless steel.

15. The cytology brush of claim 13, wherein the bristles are flexible.

16. A medical device system comprising:

a catheter comprising a lumen;

a cytology brush, wherein the cytology brush includes:

a base wire; and a plurality of bristles coupled to a distal portion of the base wire; and wherein the base wire and the cytology brush are movably positioned within the lumen of the catheter, and wherein the base wire comprises at least one loop portion that is configured to at least partially surround a portion of a guide wire to removably couple the base wire to the guide wire.

17. The medical device system of claim 16, wherein the base wire includes a bend separating first and second portions, wherein the first and second portions of the base wire are at least partially wound around each other and the base wire surrounds the guide wire at the at least one loop portion that includes a distal loop and a proximal loop; and the distal loop and the proximal loop are each formed by two half loops formed from one of the first or second portions of the base wire.

18. The medical device system of claim 17, wherein each of the first and second portions of the base wire comprise a leading end, and wherein the leading end of the first and second portions is welded to the base wire at a location proximal of a distal end of the base wire.

19. A cytology brush system comprising:

a guide wire;

a cytology brush comprising a base wire and a plurality of bristles coupled to the base wire; and a catheter comprising a lumen for receiving the cytology brush, wherein the base wire comprises at least one loop configured to at least partially surround the guide wire and removably couple the base wire to the guide wire for insertion of the cytology brush within a patient.

20. The cytology brush system of claim 19, wherein the at least one loop is a half loop configured to receive the guide wire at a non-parallel angle relative to the base wire, and the base wire further includes a gap between an extreme end of a strand of the base wire, the gap being sized with respect to the guide wire such that a distance between the extreme end and the base wire allows passage of the guide wire.

* * * * *